United States Patent
Herrera

(12)
(10) Patent No.: US 6,565,819 B1
(45) Date of Patent: May 20, 2003

(54) TOOTHBRUSH SANITIZER

(76) Inventor: Jose D. Herrera, 2520 Wassum Trail, Chuluota, FL (US) 32766

( * ) Notice: Subject to any disclaimer, the term of this patent is extended or adjusted under 35 U.S.C. 154(b) by 0 days.

(21) Appl. No.: 09/574,078

(22) Filed: May 19, 2000

(51) Int. Cl.⁷ .................................................. S61L 2/00
(52) U.S. Cl. ......................... 422/298; 422/26; 422/292; 422/297
(58) Field of Search .......................... 422/26, 297, 292, 422/298

(56) References Cited

U.S. PATENT DOCUMENTS

| | | | |
|---|---|---|---|
| 4,400,357 A | | 8/1983 | Hohmann |
| 4,414,037 A | * | 11/1983 | Friedheim |
| 4,816,648 A | * | 3/1989 | Dusbabek |
| 5,919,416 A | * | 7/1999 | Auner |
| 6,171,559 B1 | * | 1/2001 | Sanders et al. |

* cited by examiner

Primary Examiner—Krisanne Thornton
(74) Attorney, Agent, or Firm—Julian C. Renfro, Esq.

(57) ABSTRACT

A device for the rapid sanitizing of a toothbrush comprising a housing having an upper portion, a mid portion and a lower portion, with an aperture located in the mid portion of the housing for receiving the bristle portion of a toothbrush. The upper portion of the housing has a reservoir for water, and a tube is connected for carrying selected amounts of water to a pan mounted in the lower portion of the housing. The pan is configured to contain a relatively small quantity of water delivered during a relatively short interval of time from the reservoir by means of a pump driven by an electric motor. A heater is mounted closely below the pan and arranged to heat and vaporize the small quantity of water delivered to the pan at a given moment. The motor is caused to rotate during the time of the delivery of electric current to the heater, and a timer causes the rotation of the motor to cease and the shutting off of electric current to the heater after sufficient time has elapsed for the creation of heated vapor for the sanitizing of the bristles of the toothbrush inserted through the aperture.

20 Claims, 3 Drawing Sheets

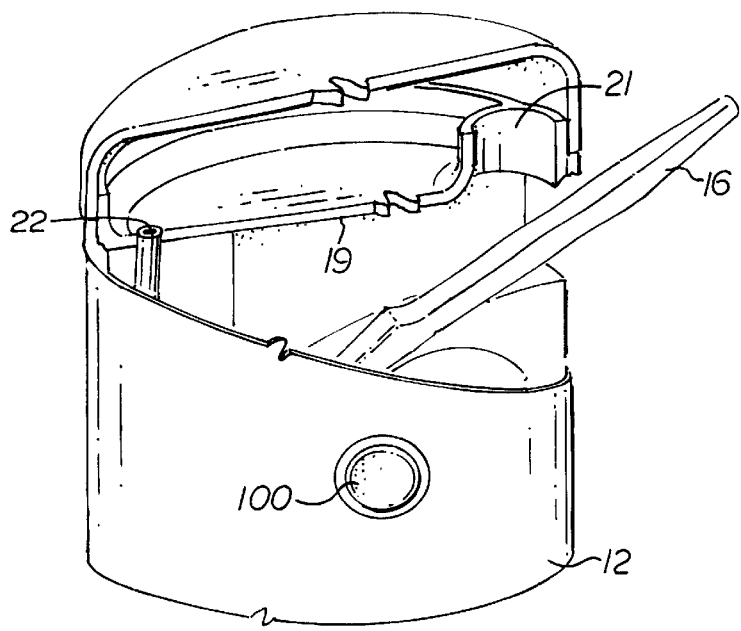
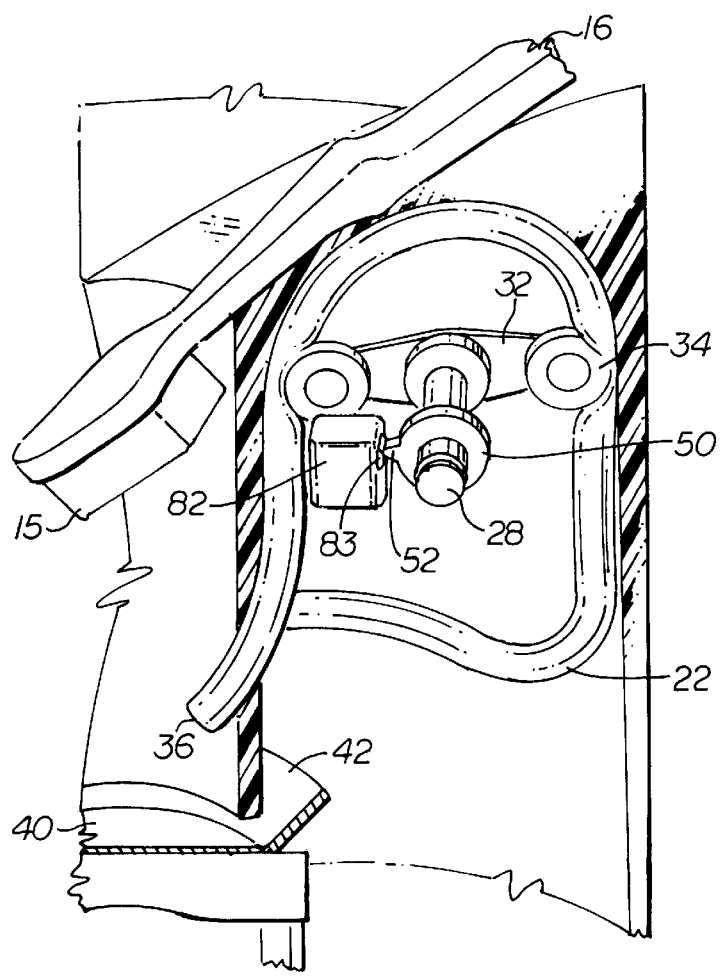

TOOTHBRUSH SANITIZER

BACKGROUND OF THE INVENTION

For some time it has been realized that the hot steam sterilizers or autoclaves employed in the medical field for sterilizing hand instruments, tools or the like require long heating and cooling times, due in part to the relatively great chamber volume of such devices.

It was accordingly proposed in the Hoffman U.S. Pat. No. 4,400,357 to provide a "Device for Sterilizing Medical and Dental Objects," with that device being small enough to be employed in the sterilization of small, hand held items, with one example being a dental hand piece. However, the Hoffman device utilized microwave radiation, with its accompanying disadvantages, with at least one of these disadvantages being the fact that many types of metal devices could not be sterilized in his device.

Somewhat similarly, the Auger U.S. Pat. No. 5,919,416 entitled "Sterilization Process for Thermoplastic Appliances" likewise entailed the use of microwave energy.

It is therefore a goal of the instant invention to provide a small, readily affordable device for sanitizing small items such as toothbrushes without necessitating the complexity and expense associated with the use of microwave energy.

SUMMARY OF THE INVENTION

In accordance with this invention I have provided a device for sanitizing a toothbrush, with this device having an aperture into which the bristle portion of a toothbrush can be inserted. In an upper portion of the housing a reservoir for water is provided, with a tube connected for carrying water from the reservoir to a pump. This pump is driven in rotation by a small electric motor contained in the housing, with the pump having an output delivered to a pan mounted in the lower portion of the housing. This pan is configured to contain a relatively small quantity of water delivered from the reservoir by the pump during a relatively short interval of time. Heater means are operatively mounted closely below the pan and arranged to heat and vaporize the small quantity of water residing in the pan at a given moment. This causes the heated vapor to flow upwardly past the bristles of the toothbrush, to bring about the sanitizing of the bristles. Means are provided for bringing about rotation of the motor essentially contemporaneously with the delivery of electric power to the heater means, so that the sanitizing procedure will be accomplished for a suitable length of time. Timing means are provided for causing the rotation of the motor to cease and the shutting off of power to the heater means after sufficient time has elapsed for the creation of a sufficient amount of heated water vapor for the sanitizing of the bristles of the toothbrush inserted through the aperture.

It is therefore a principal object of my invention to provide a compact and readily affordable device for sanitizing a small, hand held item, such as a toothbrush.

It is another object of this invention to provide a device sufficiently small as to be easily accommodated on or near the lavatory in a bathroom, with this device making it readily possible for a person to sanitize his or her toothbrush immediately before use, thus to make the ingestion of germs less likely and to cause the brushing of the teeth to be a more enjoyable procedure.

It is yet another object of this invention to provide a compact device for sanitizing the bristles of a toothbrush either before or after use, with this device advantageously being constructed utilizing inexpensive, easily obtainable components, and avoiding the use of microwave radiation.

These and other objects, features and advantages will become more apparent from a study of the appended text and the associated drawings.

BRIEF DESCRIPTION OF DRAWINGS

FIG. 2 is a fragmentary view generally along the lines of FIG. 1, but revealing the placement of the start button on the outer front portion of the housing;

FIG. 3 is a fragmentary view to a somewhat larger scale in order to reveal the utilization of a slowly rotating cam arrangement for causing an automatic cessation of the sanitizing cycle of my novel device after a relatively short time interval.

DETAILED DESCRIPTION

Figure 1:
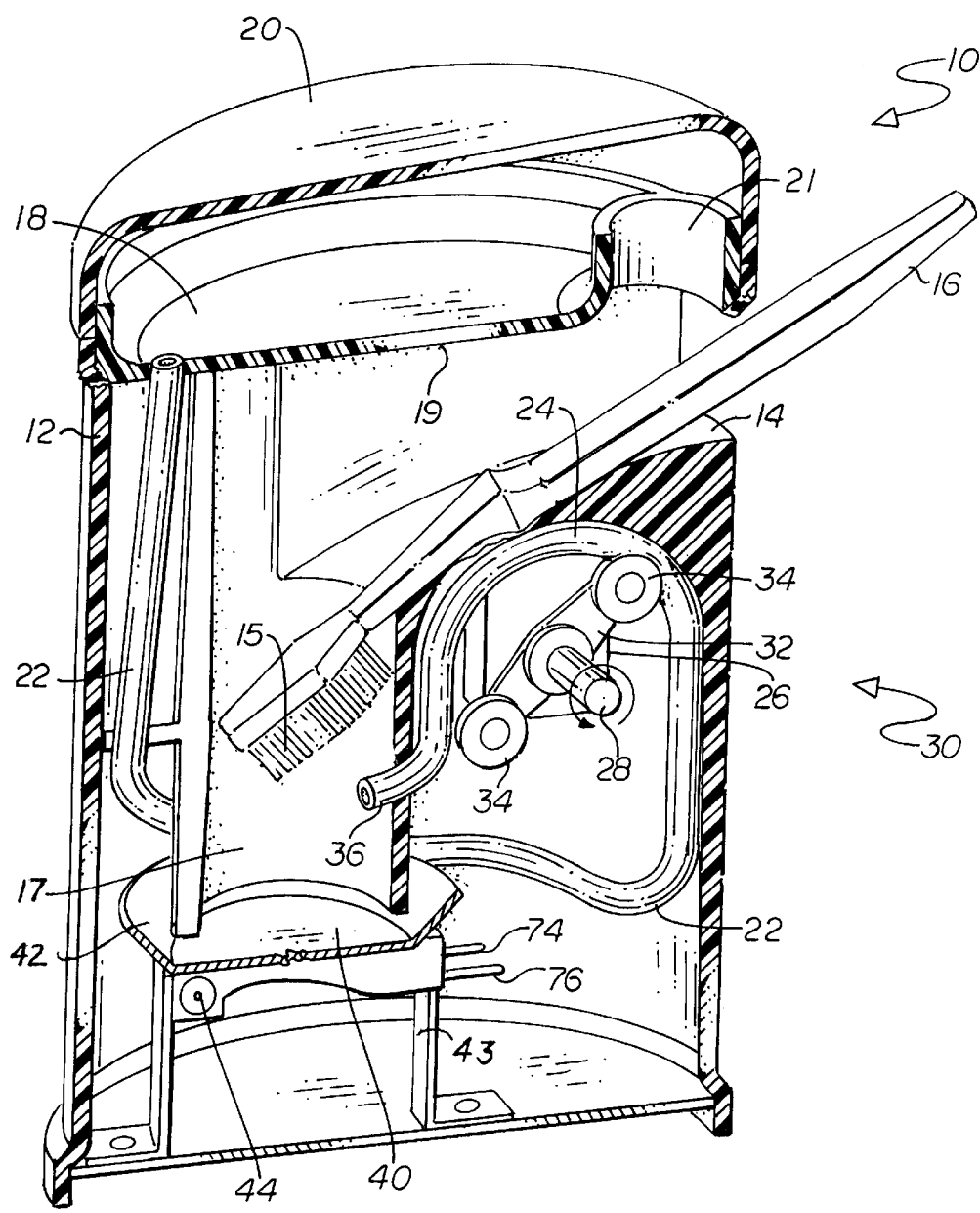
FIG. 1 is a perspective view of a preferred embodiment of my novel device, with sectioning away of portions of the housing of the device having been accomplished in order to reveal internal construction.

With initial reference to FIG. 1 it will be noted that I have illustrated my novel device 10 for sanitizing a small hand held item, such as a toothbrush. It will be seen that my device comprises a housing 12 having an upper portion, a mid portion and a lower portion, with an aperture 14 located in the mid portion of the housing. It is into this aperture that the bristle portion 15 of a toothbrush 16 to be sanitized is to be inserted. When the toothbrush has been placed in the appropriate location depicted in FIG. 1, the bristle portion 15 of the toothbrush resides in a vertically disposed chamber 17.

It is to be observed that the upper portion of the housing 12 has a reservoir 18 for water, with the reservoir being enclosed by a cap 20. A steam vent 21 is disposed in one portion of the reservoir, to make possible the recycling of the water utilized in my device. In other words, the reservoir not only represents a supply of water, but also is a body of water into which the steam can condense on contact. By removing the cap 20, it becomes readily convenient for a user to add more water to the reservoir from time to time, on an as-needed basis.

It will be noted that a tube 22 extends downwardly from a low point in the reservoir 18, with this tube being designed to convey water, under the influence of gravity, to a location where it can be pumped to a site of intended use. In this instance, the site of intended use is a pan 40 located in a lower portion of the housing 12, directly under the aforementioned vertically disposed chamber 17, which pan will be described at greater length hereinafter.

Although I am not limited to any particular type of pump for causing selected small quantities of water to be transferred, on occasion, from the reservoir 18 to the pan 40, I have found it desirable, in accordance with a preferred embodiment, to utilize a peristaltic pump 30 for conveying water from the reservoir 18 to the pan 40. It is to be understood that the tube 22 is of flexible construction, with it to be noted that a portion of the tube 22 is bent at location 24 into a curved configuration of constant radius. At a location central to the curved portion of the tube, an electric motor 26 is mounted, extending outwardly from the end of which is an elongate shaft 28. This motor is of a commercially available type and contains internal gearing such that the shaft rotates at a very low speed, such as one revolution every 60, 90 or 120 seconds. The motor may be of a type produced by HIT Technology and Industry of Brea, Calif. One particular motor is HTFYG 048-B-030H.

The aforementioned peristaltic pump 30 is formed by a rotatable member 32 having a pair of rollers 34 mounted thereon. The rotatable member 32 is affixed to the shaft 28, so as a result of shaft rotation, the rollers travel, in the present instance, in a counterclockwise direction. The rollers 34 may be regarded as being mounted at diametrically opposite locations that are equidistant from the shaft 28, with each roller being in firm and continuous contact with the tube 22 during one part or aspect of the rotation of the shaft 28.

It is to be noted that each of these rollers 34 has a grooved circumferential surface, with the radius of each such surface essentially coinciding with the radius of the tube 22. Because each of the rollers 34 is in firm, compressive contact with the tube for a certain part of the rotation of the member 32, as each roller comes into contact with the tube, it serves to move an increment of water along the interior of the tube. Ultimately, such increment of water is caused to leave the bottom end 36 of the tube, and drip onto the pan 40 residing in a lower portion of the housing 12. The pan is provided with sidewalls 42 and is supported by a plurality of legs 43 so that it will be disposed above the bottom member 46 of the housing. The pan 40 is configured to contain a relatively small quantity of water delivered during a relatively short interval of time from the reservoir 18 by the pump 30.

An important part of my invention involves the fact that a heater unit 44 is operatively mounted closely below the pan 40 and arranged to heat and vaporize the small quantity of water residing in the pan at a given moment. Electric current is applied to this heater by means of the use of suitable electric wires 74 and 76, discussed hereinafter. The aforementioned arrangement involving the low output speed motor 26 and the peristaltic pump 30 may be regarded as being a part of the timing means operative for a relatively short interval. It is during that relatively short interval of time that a certain amount of water is delivered from the reservoir 18 to the pan 40 essentially contemporaneously with the delivery of electric power to the heater unit 44.

Although I am not to be limited to any particular heating arrangement, I have found that a Calrod type heater residing in an essentially curved configuration directly below the pan 40 is an ideal way for heating the limited amount of water that at a given moment resides in the pan 40. In other words, I prefer a resistance type heater rather than a microwave type device for heating the water. It is by heating and vaporizing this limited amount of water in the pan that the bristle portion 15 of the toothbrush 16 can be warmed and sanitized at the illustrated location in the vertically disposed chamber 17.

It is to be noted that the undersurface 19 of the housing member defining the reservoir 18 is advantageously angled somewhat upwardly toward the steam vent 21, so that some of the steam rising through the vertically disposed chamber 17 will be encouraged to enter the steam vent 21 and condense inside the reservoir. Because of this construction, an effective recycling of the water utilized in my device is made readily possible, thus diminishing the need to add more water to the reservoir during regular use of my device.

Turning now to FIG. 2, it will be noted that I have provided a start button 100 on the outer surface of the housing 12, this start button being a part of a normally open switch provided for a purpose to be described in conjunction with the electrical circuitry of my device.

With reference now to FIG. 3, it is to be observed from this fragmentary view that I have shown a cam member 50 affixed to the previously-identified shaft 28, so that the cam will at all times rotate with the shaft. Mounted at one location on the circumference of the cam 50 is a strike pin or lobe 52.

Mounted closely adjacent the cam 50 is a switch 82, which may also be referred to as a stop switch. The switch 82 is mounted on the inner wall of the housing, typically adjacent the start switch, and is a normally closed switch. Operatively mounted on the outer surface of the switch 82 is an actuation button 83, with the positioning of the stop switch being such that the button 83 will be contacted by the strike pin or lobe 52 of the cam 50 at one phase of the rotation of the cam.

It is as a result of this arrangement involving the cam 50 and the switch 82 that the operation involving the sanitizing of the bristles of the toothbrush is caused to cease after an appropriate elapse of time, such as 60, 90 or 120 seconds.

In accordance with my invention, the bristles of a toothbrush are subjected to a period of steam saturation, with steam temperature and length of exposure as values in which to bring forth a germicidal effect causing the sanitization of the toothbrush. These values are derived from the Heat Sanitizing Tables utilized in the food industry. The temperatures I use will sanitize the brush while protecting the bristles from heat damage.

Figure 4:
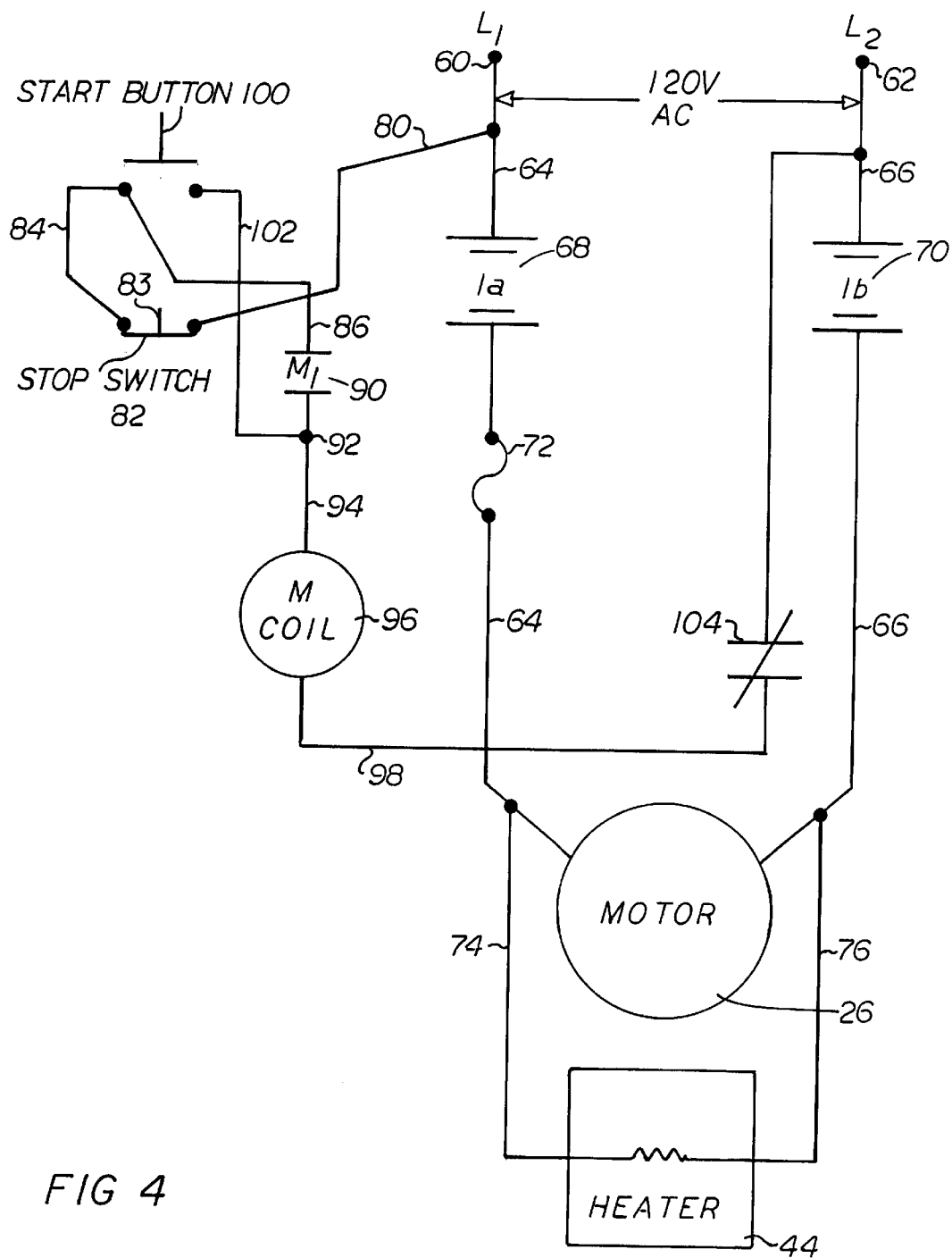
FIG. 4 is a preferred version of the circuitry utilized in connection with my invention in order to provide a reliable termination of the heating cycle subsequent to a small hand held item such as a toothbrush being sanitized.

Turning now to FIG. 4, it will be seen that I have provided electrical input leads $L_1$ and $L_2$ for the powering, when the start button 100 has been depressed, of the electric motor 26 and the heater 44. In the typical instance 110 to 120 volts AC will be applied between the terminals 60 and 62.

Connected to terminal 60 is lead 64, which is connected to a set of contacts 68, whereas connected to terminal 62 is lead 66, which is in turn connected to a set of contacts 70. Contacts 68 and 70 may be part of a commercially available multi-contact unit, and they are electrically separate, normally open contacts. By way of example, RAMCO is one manufacturer of contacts of this type, and GEMLINE is another. Obviously I am not to be limited to contacts made by either of these companies.

When the contacts 68 and 70 are closed, this brings about power being applied to motor 26, to bring about its rotation. A fuse 72 is interposed in lead 64. Also connected to lead 64 is lead 74, and connected to lead 66 is lead 76. Leads 74 and 76 supply electric power from leads $L_1$ and $L_2$ to the heater 44 at such time as power is applied to the motor 26 which, as previously indicated, is only for a relatively short time duration.

FIG. 4 reveals that lead 80 is connected to lead 64 in the vicinity of the terminal 60, with lead 80 extending to a first terminal of normally closed stop switch 82. It will be recalled from FIG. 3 that the stop switch 82 is mounted adjacent the cam 50 so that the stop button 83 will be readily accessible to be contacted by the lobe 52 of cam 50 at one phase of the cam's rotation.

Connected to a second terminal of the stop switch 82 is a lead 84 that in turn connects to terminal 86 of contact 90. Connected to a second terminal 92 of contact 90 is a lead 94 that connects to one terminal of M coil 96. Connected to the second terminal of M coil 96 is lead 98, that connects to lead 66 in the vicinity of terminal 62. This connection is made via thermal overload 104.

With regard to the start button 100, it will be noted that previously mentioned lead 84 also connects to one terminal of the normally open start button 100.

One end of a lead 102 is connected to a second terminal of the start button, with a second end of lead 102 being connected to terminal 92 of contact 90.

As a result of this arrangement, upon the operator momentarily depressing the normally open start button 100 (see FIG. 2), electric power is applied to the M coil 96 which, when energized, causes the closing of contacts 68 and 70 as well as the closing of contacts 90. The closing of contacts 68 and 70 causes, as previously mentioned, electric power to be delivered to the motor 26, to bring about rotation of same. This closing also causes electric power to be applied to the heater 44, so that it will commence vaporizing the water as it is being delivered by pump 30 to the pan 40.

Because the start button 100 is spring loaded, it returns to its normally open position when released, but because of the closing of contacts 90, coil 96 continues to remain energized as the result of voltage continuing to be applied to it via the normally closed stop switch 82.

At this point, because contacts 68, 70 and 90 remain closed, electric power leads $L_1$ and $L_2$ continue to deliver electric power to the motor 26 and heater 44. As previously explained, the operation of the motor causes water to be delivered on a substantially continuous basis to the pan 40, with the operation of the heater 44 causing the vaporization of the water in the pan, so that the heated vapor can rise up through the vertically disposed chamber 17 and bring about the sanitizing of the bristles 15 of the toothbrush.

Returning to FIG. 3, it will be recalled that the cam 50 is provided with a strike pin or lobe 52, so as a consequence of the rotation of shaft 28, the strike pin or lobe 52 is caused, in the illustrated instance, to rotate in a counterclockwise direction. Because the actuation button 83 of the stop switch 82 is positioned close to the cam 50, the strike pin or lobe 52 will cause the button 83 to be depressed upon contacting same. Upon the button 83 being depressed, the electrical contacts of the stop switch 82 open, breaking the circuit to the M coil 96.

As will be made clear from an inspection of FIG. 4, the breaking of the circuit to the M coil causes all of the previously described sets of contacts to open, with the opening of contacts 68 and 70 causing the operation of the motor 26 and the heater 44 to cease.

I have found that the momentum of the turning motor will bring the strike pin or lobe 52 to rest at a desired location in which it is no longer in contact with the actuation button 83. After the stop switch has been actuated to cause the operational cycle to cease, the spring action of the switch 82 causes its contacts to reclose, so that the circuit will be ready for reuse at such time as the start button is again depressed.

Although I have described but a single embodiment of my invention, it is to be understood that other embodiments may be apparent to those skilled in the art, and I am not to be limited to the described construction except as required by the scope of the appended claims.

I claim:

1. A device for sanitizing a toothbrush, said device comprising a housing having an upper portion, a mid portion and a lower portion, an aperture located in said mid portion of said housing, into which aperture the bristle portion of a toothbrush can be inserted, said upper portion of said housing having a reservoir for water, a tube connected for carrying water from said reservoir to a pump, said pump being driven in rotation by an electric motor contained in said housing, with said pump having an output, means delivering the output from said pump to a pan mounted in said lower portion of said housing, said pan being configured to contain a small quantity of water delivered during a short interval of time from said reservoir by said pump, heater means operatively mounted closely below said pan and arranged to heat and vaporize the small quantity of water residing in said pan at a given moment, means for bringing about rotation of said motor during the time of the delivery of electric current to said heater means, and timing means for causing the rotation of said motor to cease and the shutting off of electric current to said heater means after sufficient time has elapsed for the creation of heated vapor for the sanitizing of the bristles of the toothbrush inserted through said aperture.

2. The device for sanitizing a toothbrush as recited in claim 1 in which a vertically disposed chamber is defined above said pan, up through which the heated vapor can rise, with the bristles of the toothbrush extending into said vertically disposed chamber when the toothbrush has been inserted into said aperture located in said mid portion of said housing.

3. The device for sanitizing a toothbrush as recited in claim 1 in which said pump is a peristaltic pump.

4. The device for sanitizing a toothbrush as recited in claim 1 in which said motor has an output shaft, with said shaft geared to rotate at a low speed and to drive said pump in rotation.

5. The device for sanitizing a toothbrush as recited in claim 4 in which a part of said timing means is operatively mounted on said output shaft, to rotate therewith.

6. A device for sanitizing a toothbrush, said device comprising a housing having a sidewall, with said housing having an upper portion, a mid portion and a lower portion, a vertically disposed chamber defined in an interior part of said housing, an aperture defined in the sidewall at a mid portion of said housing, with said aperture being in communication with said vertically disposed chamber, said aperture being configured to receive a toothbrush, with the bristle portion of the toothbrush able to extend into said vertically disposed chamber, said upper portion of said housing having a reservoir for water, a tube connected for carrying water from said reservoir to a pump, said pump being driven in rotation by an electric motor contained in said housing, with said pump having an output, means delivering the output from said pump to a pan mounted in said lower portion of said housing, at a location directly below said vertically disposed chamber, said pan being configured to contain a small quantity of water delivered during a short interval of time from said reservoir by said pump, heater means operatively mounted closely below said pan and arranged to heat and vaporize the small quantity of water residing in said pan at a given moment, with the heated water vapors able to rise upwardly through said vertically disposed chamber, means for bringing about rotation of said motor essentially contemporaneously with the delivery of electric current to said heater means, and timing means for causing the rotation of said motor to cease and the shutting off of electric current to said heater means after sufficient time has elapsed for the creation of heated vapor for the sanitizing of the toothbrush inserted through said aperture.

7. The device for sanitizing a toothbrush as recited in claim 6 in which said pump is a peristaltic pump.

8. The device for sanitizing a toothbrush as recited in claim 6 in which said motor has an output shaft, with said shaft geared to rotate at a low speed and to drive said pump in rotation.

9. The device for sanitizing a toothbrush as recited in claim 8 in which a part of said timing means is operatively mounted on said output shaft, to rotate therewith.

10. The device for sanitizing a toothbrush as recited in claim 6 in which said pump is driven by a shaft extending outwardly from said motor, with a cam being mounted on said shaft, said cam being directly responsible for interacting with an electric switch serving to bring about the cessation of rotation of said motor, and turning off said heater located under said pan after a suitable heating cycle.

11. A device for cleaning and sanitizing a toothbrush, said device comprising a housing having an upper portion, a mid portion and a lower portion, an aperture located in said mid portion of said housing, into which aperture the bristle portion of a toothbrush can be inserted, said upper portion of said housing having a reservoir for water, a tube connected for carrying water from said reservoir to a pump, said pump being a peristaltic pump, with said tube being an intrinsic part of said pump, a rotative part of said pump being driven in rotation by an electric motor contained in said housing, with water being caused to flow out of a lower end of said tube as a result of the rotation of said pump, the water flowing out of the end of said tube being delivered into a pan mounted in said lower portion of said housing, said pan being configured to contain a relatively small quantity of water delivered during a relatively short interval of time from said reservoir by said pump, heater means operatively mounted closely below said pan and arranged to heat and vaporize the small quantity of water residing in said pan at a given moment, a vertically disposed chamber located above said pan, and serving to direct heated vapors onto the bristles of the toothbrush, means operative for a relatively short interval of time for bringing about rotation of said motor essentially contemporaneously with the delivery of electric current to said heater means, and timing means for causing the cessation of rotation of said motor and the shutting off of electric current to said heater means after sufficient time has elapsed for the creation of sufficient heated vapor for the sanitizing of the toothbrush inserted through said aperture.

12. The device for cleaning and sanitizing a toothbrush as recited in claim 11 in which said pump is driven by a shaft extending outwardly from said motor, with a cam being mounted on said shaft, said cam being directly responsible for interacting with an electric switch serving to bring about the cessation of rotation of said motor, and turning off said heater located under said pan after a suitably short heating cycle.

13. The device for sanitizing a toothbrush as recited in claim 11 in which a steam vent is disposed in one portion of said reservoir, to enable the water utilized in said device to be recycled and to condense so as to become a part of the water contained in said reservoir.

14. A device for sanitizing a toothbrush, said device comprising a housing having an upper portion, a mid portion and a lower portion, an Aperture located in said mid portion of said housing, into which aperture the bristle portion of a toothbrush can be inserted, with the bristle portion of the toothbrush extending into a vertically disposed chamber, said upper portion of said housing having a reservoir for water, a tube connected for carrying water from said reservoir to a pump, said pump being a peristaltic pump, with a portion of said tube forming an intrinsic part of said pump, a rotative part of said pump being driven in rotation by an electric motor contained in said housing, with water being caused to flow out of a lower end of said tube as a result of said rotative part of said pump contacting said portion of said tube, the water flowing out of the end of said tube being delivered into a pan mounted in said lower portion of said housing, said pan being disposed substantially directly below said vertically disposed chamber and being configured to contain a relatively small quantity of water delivered during a relatively short interval of time from said reservoir by said pump, heater means operatively mounted closely below said pan and arranged to heat and vaporize the small quantity of water residing in said pan at a given moment, means operative for a relatively short interval of time for bringing about rotation of said motor essentially contemporaneously with the delivery of electric current to said heater means, with this resulting in the creation of heated vapor that rises from said pan through said vertically disposed chamber to sanitize the bristles of the toothbrush, and timing means for causing the rotation of said motor to cease and the shutting off of power to said heater means after sufficient time has elapsed for the creation of heated vapor for the sanitizing of the bristles of the toothbrush inserted through said aperture.

15. The device for sanitizing a toothbrush as recited in claim 14 in which a steam vent is disposed in one portion of said reservoir, to enable the water utilized in said device to be recycled and to condense so as to become a part of the water contained in said reservoir.

16. The device for sanitizing a toothbrush as recited in claim 14 in which said pump is a peristaltic pump having rollers arranged to directly act upon said tubing.

17. The device for sanitizing a toothbrush as recited in claim 14 in which said motor has an output shaft, with said shaft geared to rotate at a very low speed and to drive said pump in rotation.

18. The device for sanitizing a toothbrush as recited in claim 14 in which an intrinsic part of said timing means is operatively mounted on said output shaft, to rotate therewith.

19. The device for sanitizing a toothbrush as recited in claim 14 in which said pump is driven by a shaft extending outwardly from said motor, with a cam mounted on said shaft, said cam being directly responsible for interacting with an electric switch serving to bring about the cessation of rotation of said motor, and turning off said heater located under said pan after a heating cycle of suitable duration.

20. The device for sanitizing a toothbrush as recited in claim 19 in which said electric switch is a normally closed switch operatively disposed in an electric circuit involving said motor and said heater means, with the interaction of said cam with said switch serving to bring about the opening of the circuit and the deprivation of electric power to said motor and heater means.

* * * * *